(12) United States Patent
Petrovskaia et al.

(10) Patent No.: US 6,736,998 B2
(45) Date of Patent: May 18, 2004

(54) INDENO-FUSED PHOTOCHROMIC NAPHTHOPYRANS

(75) Inventors: Olga G. Petrovskaia, Monroeville, PA (US); Anil Kumar, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 127 days.

(21) Appl. No.: 10/039,984

(22) Filed: Oct. 29, 2001

(65) Prior Publication Data

US 2003/0071247 A1 Apr. 17, 2003

Related U.S. Application Data

(60) Provisional application No. 60/258,973, filed on Dec. 29, 2000.

(51) Int. Cl.[7] .................. G02B 5/23; C07D 311/78
(52) U.S. Cl. .................. 252/586; 549/381; 549/382; 549/331; 549/332; 351/163; 524/110; 546/196; 544/150; 548/525
(58) Field of Search .................. 252/586; 549/381, 549/382, 331, 332; 351/163; 524/110; 546/196; 544/150; 548/525

(56) References Cited

U.S. PATENT DOCUMENTS

| | | | | |
|---|---|---|---|---|
| 4,425,403 | A | 1/1984 | Taniguchi et al. | 428/331 |
| 5,274,132 | A | 12/1993 | VanGemert | 549/389 |
| 5,645,767 | A | 7/1997 | Van Gemert | 252/586 |
| 5,698,141 | A | 12/1997 | Kumar | 252/586 |
| 5,723,072 | A | 3/1998 | Kumar | 252/586 |
| 5,955,520 | A | * 9/1999 | Heller et al. | 549/382 |
| 5,961,892 | A | 10/1999 | Gemert et al. | 252/586 |
| 6,113,814 | A | 9/2000 | Gemert et al. | 252/586 |
| 6,146,554 | A | 11/2000 | Melzig et al. | 252/586 |
| 6,296,785 | B1 | * 10/2001 | Nelson et al. | 252/586 |
| 6,315,928 | B1 | * 11/2001 | Mann et al. | 252/586 |
| 6,506,322 | B1 | * 1/2003 | Breyne | 252/586 |
| 6,506,538 | B1 | * 1/2003 | Breyne | 252/586 |

FOREIGN PATENT DOCUMENTS

| | | |
|---|---|---|
| JP | 00327675 A | 11/2000 |
| WO | WO 99/15518 | 9/1998 |

OTHER PUBLICATIONS

*Friedel–Crafts and Related Reactions*, George Olah, Interscience Publishers, 1964, vol. 3, Chapter XXXI (Aromatic Ketone Synthesis).

"Regioselective Friedel–Crafts Acylation of 1,2,3,4–Tetrahydroquinoline and Related Nitrogen Heterocycles: Effects of NH Protective Groups and Ring Size" by Ishihara, Yugi et al., J. Chem. Soc., Perkin Trans. 1, pp 3401–3406, 1992.

* cited by examiner

*Primary Examiner*—Philip C. Tucker
(74) *Attorney, Agent, or Firm*—Frank P. Mallak

(57) ABSTRACT

Described are novel reversible photochromic indenonaphthopyran compounds, examples of which are 2H-naphtho [1,2-b]pyrans characterized by having a substituted or unsubstituted indeno group fused at the 2,3 positions of the group to the 1 side of the 2H-naphthopyran. The compounds also have substituents at the 3 position of the pyran ring. Substituents may also be present at the number 5, 6, 7, 8, 9, 10, 11, 12, or 13 carbon atoms of the compounds. These compounds may be represented by the following graphic formulae:

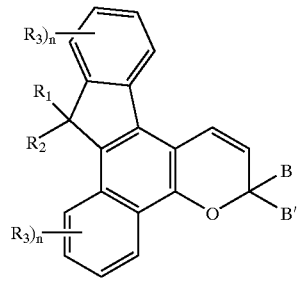

Also described are various substrates, e.g., paper, glass, organic polymeric materials, etc., that contain or that are coated with such compounds. Optically clear articles such as ophthalmic lenses or other plastic transparencies that incorporate the novel indenonaphthopyran compounds or combinations thereof with complementary photochromic compounds, e.g., indenonaphthopyrans, naphthopyrans, benzopyrans, oxazine-type compounds, etc., are also described.

21 Claims, No Drawings

INDENO-FUSED PHOTOCHROMIC NAPHTHOPYRANS

CROSS REFERENCE TO RELATED APPLICATIONS

This application claims priority to provisional application Serial No. 60/258,973 filed on Dec. 29, 2000.

DESCRIPTION OF THE INVENTION

The present invention relates to certain novel naphthopyran compounds. More particularly, this invention relates to novel indeno-fused photochromic naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion.

Indenonaphthopyrans are known and have been disclosed in U.S. Pat. Nos. 5,645,767, 5,698,141, 5,723,072, 6,113,814 and 6,146,554 and International Patent Application Publication No. WO 99/15518. In each of these disclosures, the indeno group is in a reversed position as compared to the indenonaphthopyrans of the present invention. Japan Unexamined Patent Publication P2000-327675A discloses an indenonaphthopyran in which the indeno group is substituted with fluorenyl.

The present invention relates to a naphthopyran of 2H-naphtho[1,2-b]pyran structure characterized by having a substituted or unsubstituted indeno group fused at the 2,3 positions of the group to the 1 side of the naphthopyran. The compounds also have substituents at the 3 position of the pyran ring. These compounds have unexpectedly been found to demonstrate a bathochromic shift for the wavelength in the visible spectrum at which the maximum absorption of the activated (colored) form of the photochromic compound, i.e., the lambda max (Vis), occurs, thereby resulting in activated colors ranging from yellow/brown to blue/gray. Due to the bathochromic shift, compounds of the present invention demonstrate different colors than similar compounds without an unsubstituted or substituted indeno group fused at the 2,3 position of the group to the 1 side of the napthopyran. In addition, compounds of the present invention have demonstrated a high molar absorptivity (or molar extinction coefficient) in the UV, an acceptable fade rate without the addition of acids or bases, a high activated intensity, and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Other than in the operating examples, or where otherwise indicated, all values, such as those expressing wavelengths, quantities of ingredients, ranges or reaction conditions, used in this description and the accompanying claims are understood as modified in all instances by the term "about" which means close to or near.

As used herein, the terms "halo" and "halogen" are defined to include chloro, fluoro, bromo and iodo and chlorine, fluorine, bromine and iodine, respectively. The term "aryl" is defined herein to include phenyl and naphthyl.

The disclosures of the patents and articles cited herein describing photochromic imbibition processes and compositions, procedures for making polymerizable and nonpolymerizable compounds of the present invention, complementary photochromic compounds, polymeric coatings and methods of applying such coatings, polymeric organic host materials and polymerizates are incorporated herein, in toto, by reference.

In accordance with the present invention, it has now been discovered that novel 2H-naphtho[1,2-b]pyran structures characterized by having a substituted or unsubstituted indeno group fused at the 2,3 positions of the group to the 1 side of the naphthopyran and demonstrating activated colors ranging from yellow/brown to blue/gray, an acceptable fade rate, high activated intensity and a high coloration rate may be prepared. These compounds may be described as indeno[3',2':3,4]naphtho[1,2-b]pyrans having substituents at the 3 position of the pyran ring. Substituents may also be present at the number 5, 6, 7, 8, 9, 10, 11, 12, or 13 carbon atoms of the compounds. The indeno group may be represented by the following graphic formula I' in which numbers 1 through 9 represent the ring atoms of the indeno group.

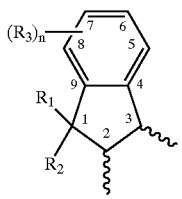

A typical 2H-naphtho[1,2-b]pyran structure is represented by the following graphic formula I″, in which the letters a through n represent the sides and X represents potential substituents known in the art.

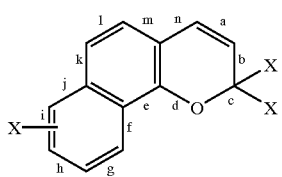

The compounds of the present invention may be represented by the following graphic formula I in which the letters a through u represent the sides of the indenonaphthopyran rings, and the numbers represent the numbers of the ring atoms of the indenonaphthopyran.

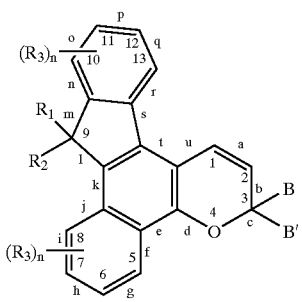

The indenonaphthopyran of the present invention is a naphthopyran compound of 2H-naphtho[1,2-b]pyran structure, such as represented by graphic formula I″, characterized by having fused to the 1 side of the 2H-naphthopyran a group represented by graphic formula I′ at the 2,3 positions of group I′. The group represented by graphic formula I′ may be unsubstituted such as when $R_1$ and $R_2$ are each hydrogen and equals 0 or may be substituted with substituents known in the art for use on photochromic compounds. Different embodiments of the compounds of the present invention are contemplated based on photochromic activity.

In graphic formulae I′, $R_1$ and $R_2$ may each be selected from the group consisting of:

(i) hydrogen, hydroxy, amino, mono- and di-substituted amino, $C_1$–$C_6$ alkyl, $C_1$–$C_6$ haloalkyl, $C_3$–$C_7$ cycloalkyl, benzyl, allyl, mono-substituted benzyl, halogen and the group, —C(O)W, wherein W is hydroxy, $C_1$–$C_6$ alkyl, $C_1$–$C_6$ alkoxy, $C_3$–$C_7$ cycloalkyloxy, phenyl, mono-substituted phenyl, phenoxy, amino, mono($C_1$–$C_6$)alkylamino, di($C_1$–$C_6$) alkylamino, morpholino, piperidino or pyrrolidyl, said amino substituents being selected from the group consisting of $C_1$–$C_6$ alkyl, phenyl, benzyl and naphthyl, said benzyl and phenyl substituents being $C_1$–$C_6$ alkyl, $C_1$–$C_6$ alkoxy, piperidino, morpholino, di($C_1$–$C_6$) alkylamino or fluoro;

(ii) unsubstituted, mono- di- and tri-substituted members selected from the group consisting of phenyl, naphthyl, phenanthryl, pyrenyl, quinolyl, isoquinolyl, benzofuranyl, thienyl, benzothienyl, dibenzofuranyl, dibenzothienyl, carbazolyl, and indolyl, said group substituents being selected from the group consisting of halogen, $C_1$–$C_6$ alkyl, $C_1$–$C_6$ alkoxy, morpholino, piperidino, pyrrolidino, amino, mono- and di-substituted amino, said amino substituents being selected from the group consisting of $C_1$–$C_6$ alkyl, phenyl, benzyl and naphthyl;

(iii) monosubstituted phenyl, having a substituent at the para position that is a linking group, —($CH_2$)$_t$— or —O—($CH_2$)$_t$—, wherein t is the integer 1, 2, 3, 4, 5 or 6, connected to an aryl group, which is a member of another photochromic naphthopyran;

(iv) a group, —$OR_5$, wherein $R_5$ is $C_1$–$C_6$ alkyl, $C_1$–$C_6$ acyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ haloalkyl, allyl, benzoyl, monosubstituted benzoyl, naphthoyl or monosubstituted naphthoyl, said benzoyl and naphthoyl group substituents being $C_1$–$C_6$ alkyl or $C_1$–$C_6$ alkoxy; or $R_5$ is the group —CH($R_6$)Q, wherein $R_6$ is hydrogen or $C_1$–$C_3$ alkyl and Q is —CN, —$CF_3$, or —$COOR_7$, and $R_7$ is hydrogen or $C_1$–$C_3$ alkyl; or $R_5$ is the group, —C(O)V, wherein V is hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$) alkoxy substituted phenylamino, said aryl group substituents being $C_1$–$C_6$ alkyl or $C_1$–$C_6$ alkoxy;

(v) a group, —CH(Q′)$_2$, wherein Q′ is —CN or —$COOR_8$, wherein $R_8$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or an unsubstituted, mono- or di-substituted aryl group, each of said aryl group substituents being $C_1$–$C_6$ alkyl or $C_1$–$C_6$ alkoxy;

(vi) a group, —CH($R_9$)G, wherein $R_9$ is hydrogen, $C_1$–$C_6$ alkyl or an unsubstituted, mono- or di-substituted aryl group, and G is hydroxy, $C_1$–$C_6$ alkoxy, aryloxy, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$) alkoxy substituted phenylamino, —$COOR_8$, —$COR_{10}$ or —$CH_2OR_{11}$, wherein $R_{10}$ is hydrogen, $C_1$–$C_6$ alkyl, an unsubstituted, mono- or di-substituted aryl group, amino, mono($C_1$–$C_6$)alkylamino, di($C_1$–$C_6$) alkylamino, phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, mono- or di($C_1$–$C_6$)alkoxy substituted diphenylamino, morpholino, or piperidino, wherein $R_{11}$ is hydrogen, —C(O)$R_8$, $C_1$–$C_6$ alkyl, $C_1$–$C_3$ alkoxy($C_1$–$C_6$)alkyl, phenyl($C_1$–$C_3$)alkyl, mono($C_1$–$C_6$)alkoxy substituted phenyl($C_1$–$C_3$)alkyl, or an unsubstituted, mono- or di-substituted aryl group, each of said aryl group substituents being $C_1$–$C_6$ alkyl or $C_1$–$C_6$ alkoxy; and (vii) a group, T, represented by the formula:

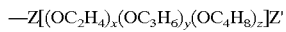

or

wherein —Z is —C(O)— or —CH$_2$—, Z' is $C_1$–$C_3$ alkoxy or a polymerizable group i.e., any functional group capable of participating in a polymerization reaction. Polymer forming methods in which the polymerizable compounds of the present invention may participate include radical polymerization, and such other polymerization processes as are described in *Ullmann's Encyclopedia of Industrial Chemistry*, "Polymerization Processes", Vol. 21A, pp 305 to 428. The polymerizable groups may be selected from the group consisting of hydroxy, (meth)acryloxy, vinyl, isocyanate and epoxy, e.g., oxiranylmethyl. When there are 2 or more polymerizable groups on the naphthopyran, they may be the same or different, x, y and z are each a number between 0 and 50, and the sum of x, y and z is between 2 and 50; or (viii) $R_1$ and $R_2$ may together form a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl, provided that said spiro-carbocyclic ring is not fluoren-9-ylidene.

In one contemplated embodiment, $R_1$ and $R_2$ are each selected from the group consisting of:

(i) hydrogen, hydroxy, $C_1$–$C_6$ alkyl, $C_1$–$C_6$ haloalkyl, di-substituted amino, $C_3$–$C_7$ cycloalkyl, benzyl, mono-substituted benzyl and the group, —C(O)W, wherein W is $C_1$–$C_6$ alkoxy, di($C_1$–$C_6$)alkylamino, morpholino or piperidino, said amino substituents being $C_1$–$C_6$ alkyl, said benzyl substituents being $C_1$–$C_6$ alkyl or $C_1$–$C_6$ alkoxy;

(ii) mono- and di and tri-substituted members selected from the group consisting of phenyl, naphthyl and dibenzofuranyl, said group substituents being selected from the group consisting of $C_1$–$C_6$ alkyl, $C_1$–$C_6$ alkoxy, and di-substituted amino, said amino substituents being $C_1$–$C_6$ alkyl;

(iii) monosubstituted phenyl, having a substituent at the para position that is a linking group, —O—(CH$_2$)$_t$—, wherein t is the integer 3, 4 or 5 connected to an aryl group, which is a member of another photochromic naphthopyran;

(iv) a group, —OR$_5$, wherein R$_5$ is $C_1$–$C_6$ alkyl, $C_1$–$C_6$ acyl, $C_1$–$C_6$ alkoxy ($C_2$–$C_4$) alkyl, benzoyl or mono-substituted benzoyl, said benzoyl substituents being $C_1$–$C_6$ alkyl or $C_1$–$C_6$ alkoxy; or R$_5$ is the group —CH(R$_6$)Q, wherein R$_6$ is hydrogen and Q is —COOR$_7$, and R$_7$ is $C_1$–$C_3$ alkyl; or R$_5$ is the group, —C(O)V, wherein V is $C_1$–$C_6$ alkoxy or di($C_1$–$C_6$) alkyl amino;

(v) a group, —CH(Q')$_2$, wherein Q' is —COOR$_8$, wherein R$_8$ is $C_1$–$C_6$ alkyl, or phenyl($C_1$–$C_3$)alkyl;

(vi) a group, —CH(R$_9$)G, wherein R$_9$ is $C_1$–$C_6$ alkyl, and G is $C_1$–$C_6$ alkoxy, —COOR$_8$—COR$_{10}$, or —CH$_2$OR$_{11}$, wherein R$_{10}$ is $C_1$–$C_6$ alkyl, di($C_1$–$C_6$) alkylamino, morpholino or piperidino; wherein R$_{11}$ is $C_1$–$C_6$ alkyl or $C_1$–$C_3$ alkoxy($C_1$–$C_6$) alkyl, and (vii) a group, T, represented by the formula:

wherein Z' is $C_1$–$C_3$ alkoxy or a polymerizable group, x, y and z are each a number between 0 and 50, and the sum of x, y and z is between 2 and 50; or (viii) $R_1$ and $R_2$ may together form an oxo group or a substituted or unsubstituted spiro-heterocyclic group containing 1 or 2 oxygen atoms and 3 to 6 carbon atoms including the spirocarbon atom, said spiro-heterocyclic ring being annellated with 1 or 2 benzene rings, said substituent being $C_1$–$C_6$ alkyl.

In another contemplated embodiment, $R_1$ and $R_2$ are each selected from the group consisting of:

(i) hydrogen, hydroxy, $C_1$–$C_3$ alkyl and the group, —C(O)W, wherein W is $C_1$–$C_6$ alkoxy,;

(ii) unsubstituted, and mono-substituted phenyl, said phenyl substituents being selected from the group consisting of $C_1$–$C_6$ alkoxy, and di-substituted amino, said amino substituents being $C_1$–$C_3$ alkyl;

(iii) monosubstituted phenyl, having a substituent at the para position that is a linking group, —O—(CH$_2$)$_t$—, wherein t is the integer 3, connected to an aryl group, which is a member of another photochromic naphthopyran;

(iv) a group, —OR$_5$, wherein R$_5$ is $C_1$–$C_6$ alkyl, $C_1$–$C_6$ alkoxy($C_2$–$C_4$)alkyl, the group —CH(R$_6$)Q, wherein R$_6$ is hydrogen or $C_1$–$C_3$ alkyl and Q is —COOR$_7$, and R$_7$ is $C_1$–$C_3$ alkyl or R$_5$ is the group, —C(O)V, wherein V is $C_1$–$C_6$ alkoxy;

(v) a group, —CH(Q')$_2$, wherein Q' is —COOR$_8$, wherein R$_8$ is $C_1$–$C_6$ alkyl;

(vi) a group, —CH(R$_9$)G, wherein R$_9$ is $C_1$–$C_6$ alkyl, and G is $C_1$–$C_6$ alkoxy, —COOR$_8$, —COR$_{10}$ or —CH$_2$OR$_{11}$ wherein R$_{10}$ and R$_{11}$ are each $C_1$–$C_6$ alkyl; and (vii) a group, T, represented by the formula:

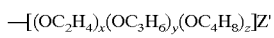

wherein Z' is $C_1$–$C_3$ alkoxy or a polymerizable group, x, y and z are each a number between 0 and 50, and the sum of x, y and z is between 2 and 50; or (viii) $R_1$ and $R_2$ may together form a substituted or unsubstituted spiro-heterocyclic group containing 1 oxygen atom and 6 carbon atoms including the spirocarbon atom, said spiro-heterocyclic ring being annellated with 2 benzene rings, said substituents being $C_1$–$C_3$ alkyl.

R$_3$ may be selected from the group of substituents known in the art for use on photochromic compounds. Each R$_3$ in graphic formula I may independently be selected from the group consisting of hydrogen, $C_1$–$C_6$ alkyl, $C_1$–$C_6$ alkoxy, $C_3$–$C_7$ cycloalkyl, phenyl, benzyl, di($C_1$–$C_6$)alkylamino, dicyclohexylamino, diphenylamino, piperidyl, morpholinyl, pyridyl, halogen, a group, T, and the group —C(O)W and n is the integer 0, 1, or 2; or when n is at least 2, and the R$_3$ substituents are adjacent, the pair of substituents forms a substituted or unsubstituted fused carbocyclic or heterocyclic ring selected from the group consisting of benzo, pyridino, pyrazino, pyrimidino, furano, dihydrofurano, 1,3-dioxolo, 1,4-dioxolo, 1,3-dioxino, 1,4-dioxino, thiopheno, benzofuro, benzothieno, indolo, and indeno, the substituents of said fused carbocyclic or heterocyclic ring being selected from the group consisting of halogen, $C_1$–$C_6$ alkyl, $C_1$–$C_6$ alkoxy, amino, mono- and di-substituted amino, said amino substituents being selected from the group consisting of $C_1$–$C_6$ alkyl, phenyl, benzyl and naphthyl; said first $R_3$ ring being fused to the o, p or q side and said second $R_3$ ring being fused to the g, h, or i side of the naphthopyran.

In one contemplated embodiment, each $R_3$ is selected from the group consisting of hydrogen, $C_1$–$C_6$ alkyl, $C_1$–$C_6$ alkoxy, di($C_1$–$C_6$)alkylamino, piperidyl, morpholinyl, pyrrolidyl, halogen, a group, T, or the group, —C(O)W and n is the integer 0, 1, or 2; or when n is 2, and the $R_3$ substituents are adjacent, a pair of substituents forms a substituted or unsubstituted fused carbocyclic or heterocyclic ring selected from the group consisting of benzo, dihydrofurano and benzofuro, the substituents of said fused carbocyclic or heterocyclic ring being selected from the group consisting of $C_1$–$C_6$ alkyl, $C_1$–$C_6$ alkoxy, and di-substituted amino, said amino substituents being $C_1$–$C_6$ alkyl; said $R_3$ ring being fused to the o, p or q sides of the naphthopyran.

In another contemplated embodiment, each $R_3$ is selected from the group consisting of hydrogen $C_1$–$C_6$ alkyl, $C_1$–$C_6$ alkoxy, morpholinyl, a group, T, and the group —C(O)W, and when m is 2 and the $R_3$ substituents are adjacent, the pair of substituents forms a substituted or unsubstituted fused carbocyclic or heterocyclic ring selected from the group consisting of benzo and benzofuro, the substituents of said fused carbocyclic or heterocyclic ring being $C_1$–$C_6$ alkoxy; said $R_3$ ring being fused to the p side of the naphthopyran.

In graphic formula I, $R_1$, $R_2$ and each $R_3$ are the same as described hereinbefore for graphic formula I'. In the definitions of $R_1$, $R_2$, $R_3$, B and B', like substituents have like meanings.

B and B' in graphic formula I may each be selected from the group of substituents known in the art for use on photochromic compounds. Specifically, B and B' may each be selected from the group consisting of:

(i) mono-T-substituted phenyl
(ii) an unsubstituted, mono-, di-, and tri-substituted aryl group;
(iii) 9-julolidinyl and an unsubstituted, mono- or di-substituted heteroaromatic group selected from the group consisting of pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and heteroaromatic substituents in (ii) and (iii) being selected from the group consisting of hydroxy, aryl, i.e., phenyl and naphthyl, mono($C_1$–$C_6$)alkoxyaryl, di($C_1$–$C_6$)alkoxyaryl, mono($C_1$–$C_6$)alkylaryl, di($C_1$–$C_6$)alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, aryl($C_1$–$C_6$ alkyl)amino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrryl, pyrrolidyl, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen;

(iv) an unsubstituted or mono-substituted member selected from the group consisting of pyrazolyl, imidazolyl, pyrazolinyl, imidazolinyl, pyrrolinyl, phenothiazinyl, phenoxazinyl, phenazinyl and acridinyl, each of said substituents being selected from the group consisting of $C_1$–$C_6$ alkyl, $C_1$–$C_6$ alkoxy, phenyl, and halogen;

(v) monosubstituted phenyl, having a substituent at the para position that is a linking group, —$(CH_2)_t$— or —O—$(CH_2)_t$—, wherein t is the integer 1, 2, 3, 4, 5 or 6, connected to an aryl group, which is a member of another photochromic naphthopyran;

(vi) a group represented by one of the following graphic formula IIA or IIB:

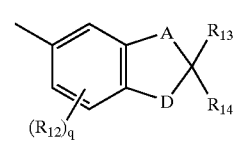

IIA

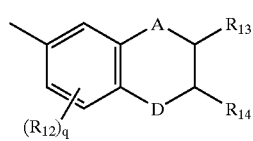

IIB wherein A is methylene or oxygen and D is oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{12}$ is $C_1$–$C_6$ alkyl, $C_1$–$C_6$ alkoxy, hydroxy, or halogen; $R_{13}$ and $R_{14}$ are each hydrogen or $C_1$–$C_6$ alkyl; and q is the integer 0, 1, or 2;

(vii) $C_1$–$C_6$ alkyl, $C_1$–$C_6$ haloalkyl, $C_1$–$C_6$ alkoxy($C_1$–$C_4$) alkyl, $C_3$–$C_6$ cycloalkyl, mono($C_1$–$C_6$)alkoxy($C_3$–$C_6$) cycloalkyl, mono($C_1$–$C_6$)alkyl($C_3$–$C_6$)cycloalkyl, halo ($C_3$–$C_6$)cycloalkyl, and $C_4$–$C_{12}$ bicycloalkyl; and (viii) a group represented by the following graphic formula IIC:

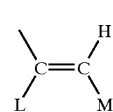

IIC wherein L is hydrogen or $C_1$–$C_4$ alkyl and M is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, or halogen.

Alternatively, B and B' may together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, and halogen.

In one contemplated embodiment, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIA and IIB, wherein A is methylene and D is oxygen, $R_{12}$ is $C_1$–$C_3$ alkyl or $C_1$–$C_3$ alkoxy, $R_{13}$ and $R_{14}$ are each hydrogen or $C_1$–$C_4$ alkyl; and q is the integer 0 or 1; (iv) $C_1$–$C_4$ alkyl; and (v) the group represented by the graphic formula IIC wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

In another contemplated embodiment, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, $C_1$–$C_3$ alkyl, $C_1$–$C_3$ alkoxy, piperidino and morpholino; and (iii) the group represented by graphic formula IIA, wherein A is methylene and D is oxygen, $R_{12}$ is $C_1$–$C_3$ alkyl or $C_1$–$C_3$ alkoxy, $R_{13}$ and $R_{14}$ are each hydrogen or $C_1$–$C_3$ alkyl, and q is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula I having certain of the substituents $R_1$–$R_3$, B and B' described hereinbefore, may be prepared by the following Reactions A through G. Methods for the preparation of compounds wherein $R_1$, $R_2$, B and/or B' is the polyalkoxylated group T are described in U.S. Pat. No. 5,961,892. Methods for the preparation of compounds wherein $R_1$, $R_2$, B and/or B' is the polymerizable polyalkoxylated group T are described in U.S. Pat. No. 6,113,814.

With reference to the following reactions, compounds represented by graphic formula V or VA are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B). R and R' represent possible substituents, as described hereinbefore with respect to B and B' of graphic formula I.

REACTION A

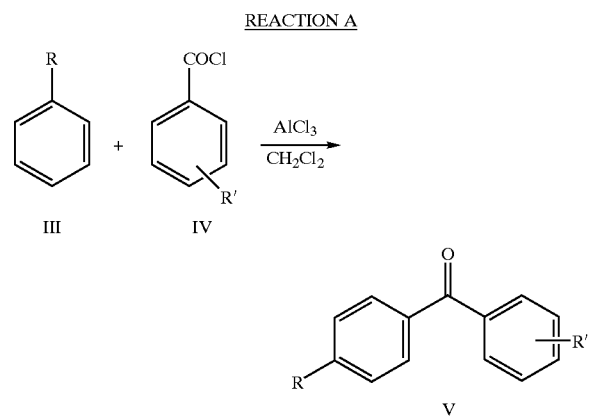

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound, e.g., 9-julolidinyl. Propargyl alcohols having a B or B' group represented by graphic formula IIC may be prepared by the methods described in U.S. Pat. No. 5,274,132, column 2, lines 40 to 68.

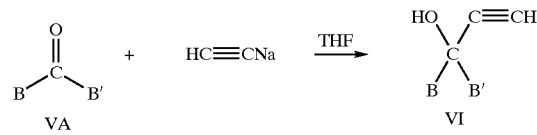

In Reaction C, a substituted or unsubstituted α-methoxy naphthalene represented by graphic formula VII is reacted with a benzoyl chloride (IV) in the presence of anhydrous aluminum chloride to form a naphthophenone represented by graphic formula VIII. Compound VIII is reacted with an organometallic compound containing $R_1$ to give a carbinol compound represented by graphic formula IX. Compound IX is heated with phosphoric acid to produce the ketone represented by graphic formula X. Compound X is aromatized by reaction with a base such as KOH in a water/ethanol mixture to produce the indeno-fused naphthol of graphic formula XI.

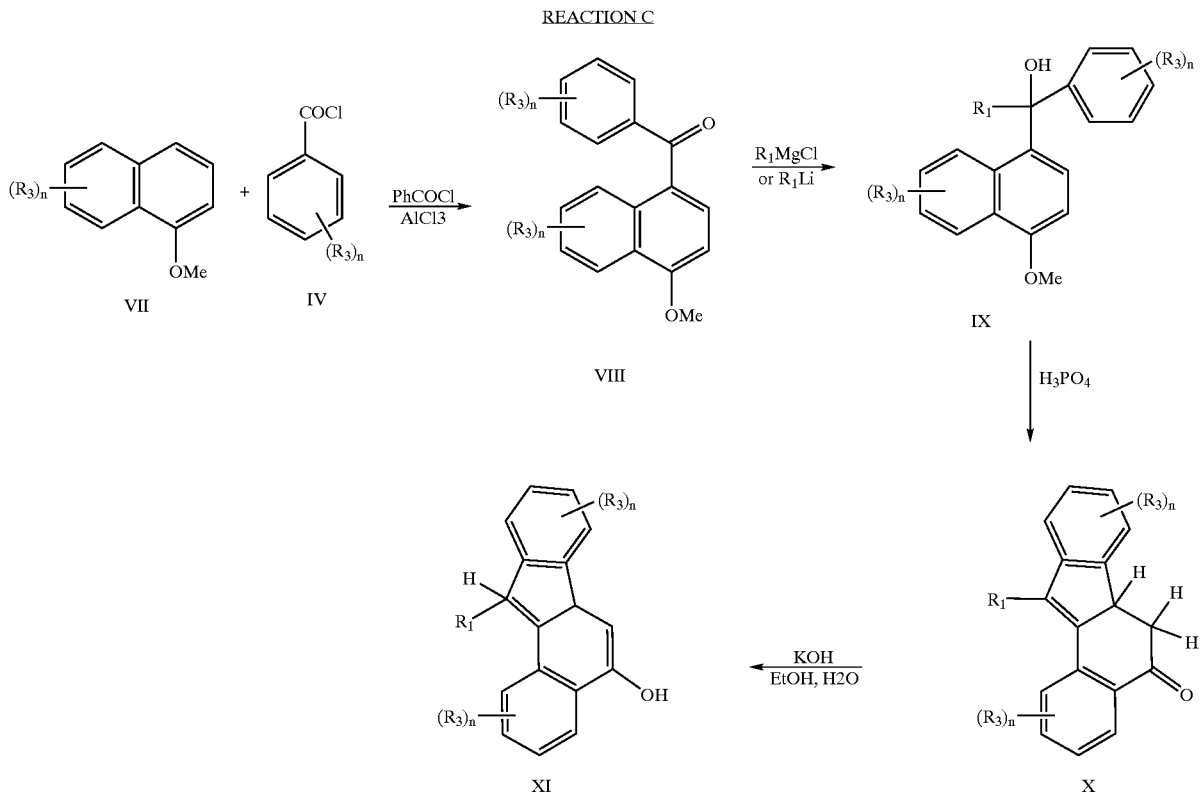

In Reaction D, an ortho bromo acetophenone represented by graphic formula XII is reacted with ethyl, α-benzoylacetate represented by graphic formula XIII in the presence of sodium hydride and cuprous bromide to form a naphthol represented by graphic formula XIV. Naphthol XIV is then hydrolyzed with aqueous base followed by cyclization in strong acid such as phosphoric acid to produce the indeno-fused naphthol represented by graphic formula XV.

REACTION D

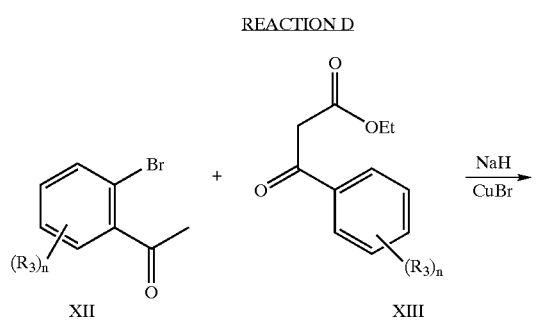

In Reaction E, the naphthol represented by graphic formula XI is coupled with a propragyl alcohol (VI) in the presence of a catalytic amount of a acid such as p-dodecylbenzene sulfonic acid to form an indenonaphthopyran represented by graphic formula IA. Compound IA is reacted with a strong base such as butyl lithium or KOH and followed by reaction with alkyl halide to produce the indenonaphthopyran represented by graphic formula IB.

REACTION E

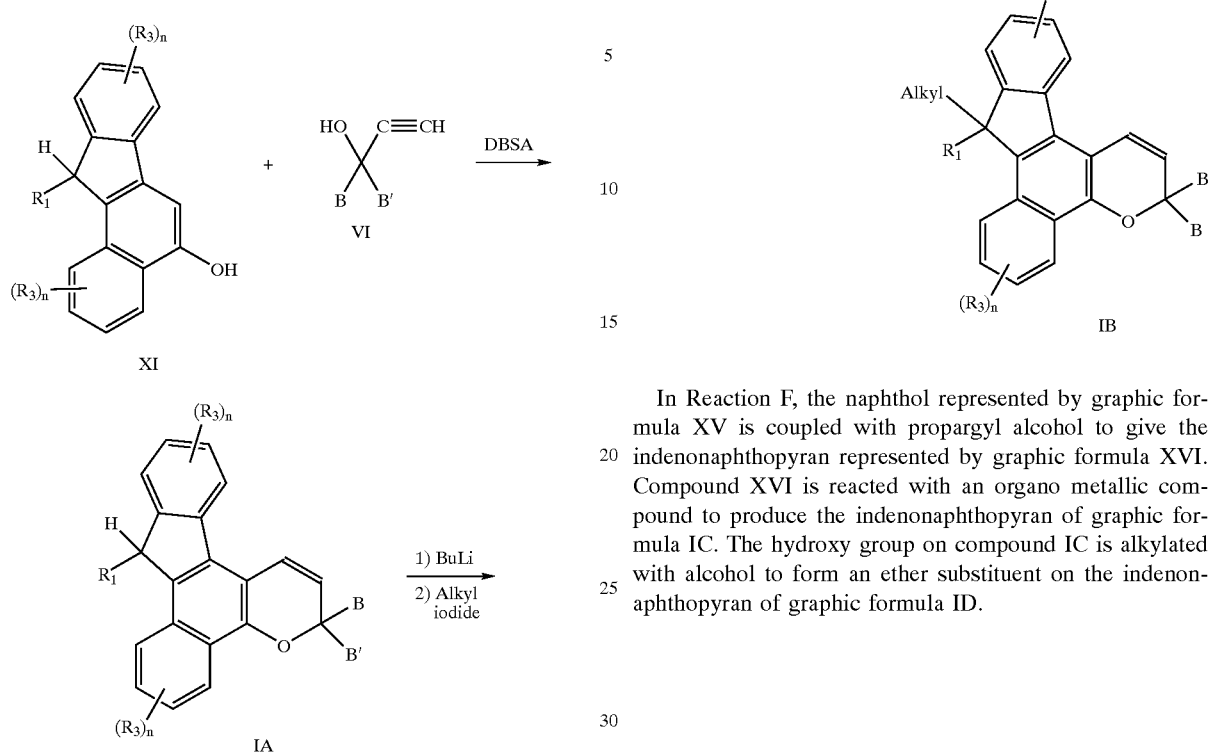

In Reaction F, the naphthol represented by graphic formula XV is coupled with propargyl alcohol to give the indenonaphthopyran represented by graphic formula XVI. Compound XVI is reacted with an organo metallic compound to produce the indenonaphthopyran of graphic formula IC. The hydroxy group on compound IC is alkylated with alcohol to form an ether substituent on the indenonaphthopyran of graphic formula ID.

REACTION F

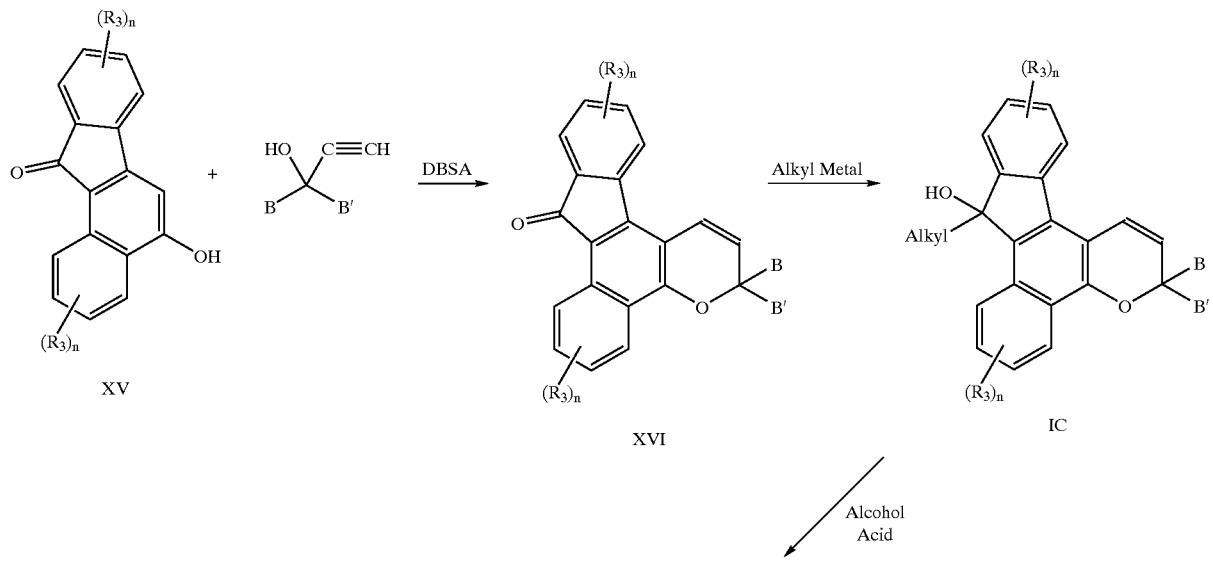

-continued

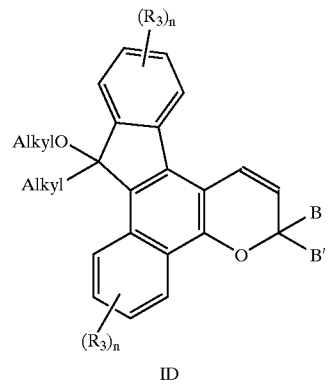

ID

In Reaction G, the ortho bromoacetophenone represented by graphic formula XII is reacted with diethyl malonate represented by graphic formula XVII in the presence of sodium hydride and cuprous bromide to form a dihydroxy naphthalene represented by graphic formula XVIII. Compound XVIII is coupled with a propargyl alcohol (VI) to produce the naphthopyran represented by graphic formula IXX. Compound IXX is methylated with methyl iodide in the presence of potassium carbonate to form the naphthopyran represented by graphic formula XX. The reaction of the aryl Grignard reagent represented by graphic formula XXI with compound XX produces the naphthopyran represented by graphic formula XXII. Compound XXII is reacted with alkyl lithium to produce a carbinol derivative represented by graphic formula XXIII. Cyclization of Compound XXIII with acid forms the desired indenonaphthopyran represented by graphic formula IE.

REACTION G

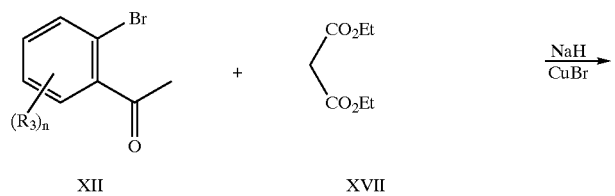

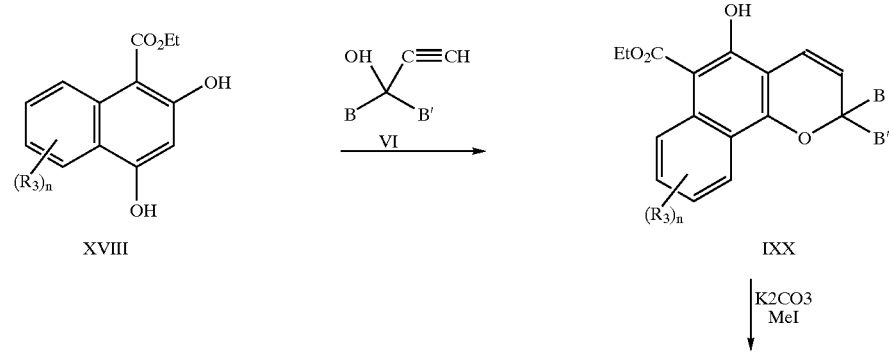

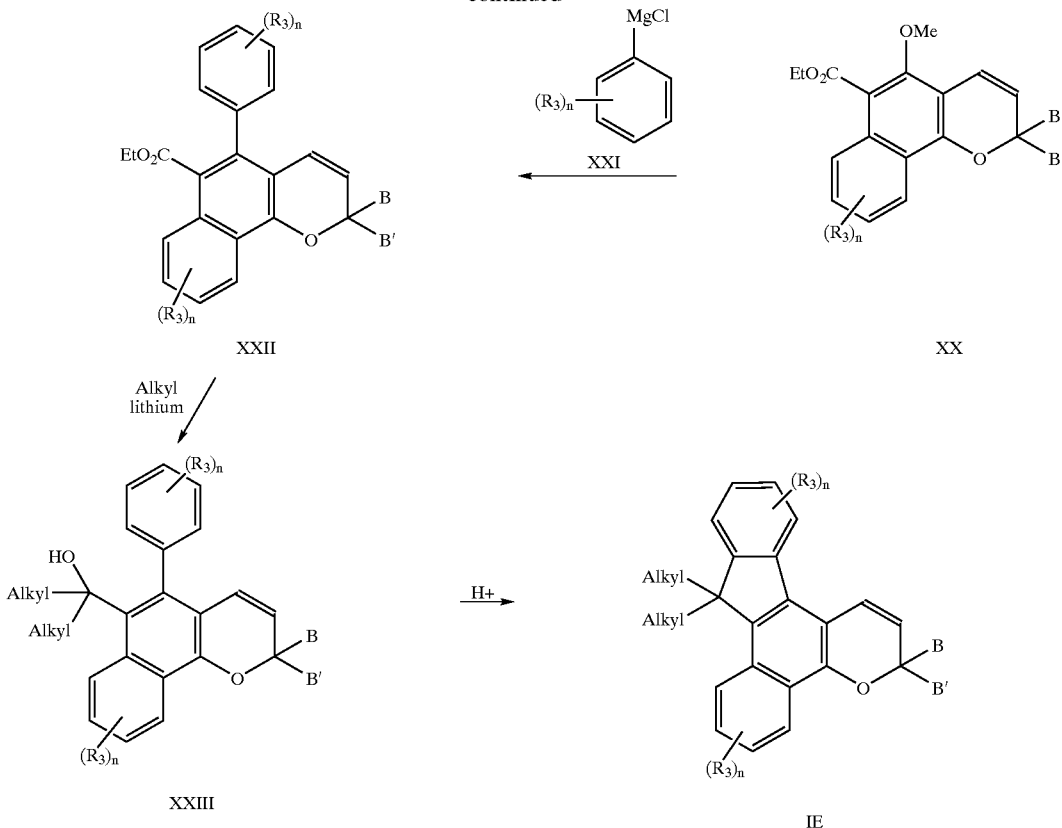

Compounds represented by graphic formula I may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions As used herein, coating compositions are defined herein to include polymeric coating compositions prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates. Potential substrates for coating compositions containing the compounds of the present invention include paper, glass, ceramics, wood, masonry, textiles, metals and polymeric organic materials.

Coating compositions may be used to produce coatings on optical elements, verification marks on security documents, e.g., documents such as banknotes, passport and drivers' licenses, for which authentication or verification of authenticity may be desired. The indenonaphthopyrans represented by graphic formula I exhibit color changes from colorless to colors ranging from yellow/brown to blue/gray.

Examples of indenonaphthopyran compounds within the scope of the invention are the following:

(a) 3,3,9-triphenyl-3H-9H-indeno[3',2':3,4]naphtho[1,2-b]pyran;
(b) 3,3-di(4-methoxyphenyl)-9-phenyl-3H-9H-indeno[3',2':3,4]naphtho[1,2-b]pyran;
(c) 3-(4-methoxyphenyl)-3,9-diphenyl-3H-9H-indeno[3',2':3,4]naphtho[1,2-b]pyran;
(d) 3-(4-morpholinophenyl)-3,9-diphenyl-3H-9H-indeno[3',2':3,4]naphtho[1,2-b]pyran;
(e) 3,3-di(4-methoxyphenyl)-9-(3-methoxyphenyl)-11-methoxy-3H-9H-indeno[3',2':3,4]naphtho[1,2-b]pyran;
(f) 3-(4-methoxyphenyl)-3-phenyl-9-(3-methoxyphenyl)-11-methoxy-3H-9H-indeno[3',2':3,4]naphtho[1,2-b]pyran;
(g) 3-(4-methoxyphenyl)-3-phenyl-9-methyl-11-methoxy-9-(3-methoxyphenyl)-3H-9H-indeno[3',2':3,4]naphtho[1,2-b]pyran;
(h) 3,3-di(4-methoxyphenyl)-9-methyl-11-methoxy-9-(3-methoxyphenyl)-3H-9H-indeno[3',2':3,4]naphtho[1,2-b]pyran;
(i) 3,3-di(4-methoxyphenyl)-9-methyl-11-methoxy-3H-9H-indeno[3',2':3,4]naphtho[1,2-b]pyran;
(j) 3,3-di(4-methoxyphenyl)-9,9-dimethyl-11-methoxy-3H-9H-indeno[3',2':3,4]naphtho[1,2-b]pyran;
(k) 3-(4-methoxyphenyl)-3-phenyl-9,9-dimethyl-11-methoxy-3H-9H-indeno[3',2':3,4]naphtho[1,2-b]pyran;
(l) 3,3-di(4-methoxyphenyl)-9,9-dimethyl-7,11-dimethoxy-3H-9H-indeno[3',2':3,4]naphtho[1,2-b]pyran;
(m) 3-(4-methoxyphenyl)-3-phenyl-9,9-dimethyl-7,11-dimethoxy-3H-9H-indeno[3',2':3,4]naptho[1,2-b]pyran;
(n) 3-(4-morpholinophenyl)-3-phenyl-9,9-dimethyl-7,11-dimethoxy-3H-9H-indeno[3',2':3,4]naphtho[1,2-b]pyran;
(o) 3,3-di(4-methoxyphenyl)-9-methyl-11,13-dimethoxy-3H-9H-indeno[3',2':3,4]naphtho[1,2-b]pyran;

(p) 3-(4-methoxyphenyl)-3-phenyl-9-methyl-11,13-dimethoxy-3H-9H-indeno[3',2':3,4]naphtho[1,2-b]pyran;

(q) 3-(4-methoxyphenyl)-3-phenyl-9,9-dimethyl-3H-9H-benzo[4",5"]indeno[3',2':3,4]naphtho[1,2-b]pyran; and (r) 3,3-di(4-methoxyphenyl-9,9-dimethyl-11-fluoro-3H-9H-indeno[3',2':3,4]naphtho[1,2-b]pyran.

It is contemplated that the photochromic indenonaphthopyrans of the present invention may each be used alone or in combination with other indenonaphthopyrans of the present invention. Alternatively, the photochromic indenonaphthopyrans of the present invention may be used in combination with one or more other appropriate complementary organic photochromic materials, i.e., organic photochromic compounds having at least one activated absorption maxima within the range of between 400 and 700 nanometers, or substances containing the same. The photochromic compounds may be incorporated, e.g. dissolved or dispersed, in a polymeric organic host material used to prepare photochromic articles which color when activated to an appropriate hue. The complementary organic photochromic materials may include indenonaphthopyrans, naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, organo-metaldithizonates, e.g. mercury dithizonates, fulgides, fulgimides and mixtures of such photochromic compounds. Such photochromic compounds are described in U.S. Pat. Nos. 5,645,767 and 6,153,126.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic indenonaphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from 0.05 to 2.0, e.g., from 0.2 to 1.0, milligrams per square centimeter of surface to which the photochromic compound is incorporated or applied. The amount of photochromic material incorporated into a coating composition may range from 0.1 to 40 weight percent based on the weight of the liquid coating composition.

The photochromic indenonaphthopyrans of the present invention may be associated with the host material by various methods described in the art. See, for example, column 13, lines 40 to 58 of U.S. Pat. No. 5,645,767. Aqueous or organic solutions or dispersions of the photochromic compounds may be used to incorporate the photochromic compounds into a polymeric organic host material or other materials such as textiles and coating compositions. Coating compositions may be applied to the substrate using a coating process such as that described in U.S. Pat. Nos. 3,971,872, 6,025,026 and 6,150,430.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The polymeric coating composition includes compositions resulting in thermoplastic or thermosetting coatings, which are described in the *Kirk-Othmer Encyclopedia of Chemical Technology,* Fourth Edition, Volume 6, pages 669 to 760. The coating may comprise at least one polymer selected from the group consisting of polyurethanes, melamine resins, polyvinyl alcohol, polyacrylates, polymethacrylates, polyamide resins and epoxy resins. Such polymer-forming coating compositions are described in U.S. Pat. No. 4,425,403.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic indenonaphthopyrans of the present invention with optical organic resin monomers used to produce optically clear coatings and polymerizates, i.e., materials suitable for optical applications, such as for example plano and ophthalmic lenses, windows, and automotive transparencies. Such optically clear polymerizates may have a refractive index that may range from 1.48 to 1.75, e.g., from 1.495 to 1.66.

Specifically contemplated are polymerizates of optical resins sold by PPG Industries, Inc. under the CR-designation, e.g., CR-307, CR-407 and CR-607, and polymerizates prepared for use as hard or soft contact lenses. Methods for producing both types of contact lenses are disclosed in U.S. Pat. No. 5,166,345, column 11, line 52, to column 12, line 52. Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631.

The present invention is more particularly described in the following examples, which are intended as illustrative only, since numerous modifications and variations therein will be apparent to those skilled in the art.

EXAMPLE 1

Step 1

1-Methoxynaphthalene (100 grams), 108 grams of benzoyl chloride and 600 milliliters (mL) of methylene chloride were mixed in a dry round bottom flask and stirred at 3–5° C. Anhydrous aluminum chloride (100 grams) was slowly added to the reaction mixture and stirred for 2 hours. The reaction mixture was poured into a 2 liter 10% hydrochloric acid/ice mixture and stirred for a half hour. The organic layer was separated, washed with water and then by 5 weight percent NaOH aqueous solution and again washed with water. The organic layer was dried over magnesium sulfate and filtered. The filtrate was concentrated and crystallized from hexane to give 160 grams of a solid product. The Nuclear Magnetic Resonance (NMR) analysis showed the product to have a structure consistent with phenyl 1-(4-methoxynaphthyl) methanone.

Step 2

Phenyl 1-(4-methoxynaphthyl)methanone (3.5 grams, 13.3 millimoles) was dissolved in 60 mL of anhydrous tetrahydrofuran under the atmosphere of nitrogen in a reaction flask, and the reaction mixture was cooled to −5° C. Excess phenyl lithium (1.8 M solution, 14.3 mL) was added dropwise, with stirring, and the reaction mixture was stirred overnight. The reaction mixture was quenched with water and acidified to a pH of 7 with 2 Normal (N) aqueous hydrochloric acid (HCl). The organic phase was separated, the solvents were removed to quantitatively yield a yellow solid. Mass Spectroscopy and Proton NMR analysis showed the product to have a structure consistent with diphenyl-(1-(4-methoxy)naphthyl)methanol.

Step 3

Diphenyl-(1-(4-methoxy)-naphthyl)methanol (2.39 grams, 7.03 millimole) was added, with stirring, to a reaction flask containing preboiled o-phosphoric acid (50 mL). The reaction mixture was heated to 100° C. over a period of 50 minutes. The reaction mixture was poured onto ice. The resulting organic precipitate was separated by filtration and washed with water. The aqueous phase was extracted with ethyl acetate. The ethyl acetate phase was separated and dried over anhydrous magnesium sulfate. The solvent was removed under reduced pressure. The organic solids were combined to yield a yellowish solid that was taken on to the next step without further purification. The Mass spectroscopy, Proton and Carbon-13 NMR analysis showed the product to have a structure consistent with 7-phenyl-1,11b-dihydrobenzyl(a)fluoren-2-one.

Step 4

The yellow solid from Step 3 was added to a reaction flask containing toluene (100 mL) A solution of potassium hydroxide (1.75 grams) in 95% ethanol (50 mL) was added, and the reaction mixture was boiled for an hour. The organic solvents were removed under reduced pressure, ethyl acetate was added, and the mixture was washed with 2 N aqueous HCl to quench the residual base. The organic phase was separated and dried over anhydrous sodium sulfate, the solvent was removed under reduced pressure, and the residual oil was crystallized from hexanes to yields 1.85 grams of a brown powder. NMR analysis showed the product to have a structure consistent with 7-phenyl-benzo(a)fluoren-2-ol.

Step 5

7-Phenyl-benzo(a)fluoren-2-ol from Step 4 (0.4 gram) was added to a reaction flask containing 40 mL of chloroform. A catalytic amount of p-dodecylbenzene sulfonic acid (approximately 20 milligrams) was added, followed by 1,1-diphenyl-2-propyn-1-ol (0.21 gram) and the reaction mixture was stirred at ambient temperature for 24 hours. The solvent was removed under reduced pressure. The reaction mixture was separated by column chromatography using as the eluant a 1:2 mixture of dichloromethane:hexanes. The top fraction was collected. The solvent was removed by evaporation and the residue was triturated with methanol to yield 0.21 gram of a light pink solid. The Proton and Carbon-13 NMR and MS analysis showed the product to have a structure consistent with 3,3,9-triphenyl-3H-9H-indeno[3',2':3,4]naphtho[1,2-b]pyran.

EXAMPLE 2

The procedure of Example 1 was followed except that in Step 5, 1,1-bis(4-methoxyphenyl)-2-propyn-1-ol was used in place of 1,1-diphenyl-2-propyn-1-ol to produce the desired product. NMR analysis showed the product to have a structure consistent with 3,3-di(4-methoxyphenyl)-9-phenyl-3H-9H-indeno[3',2':3,4]naphtho[1,2-b]pyran.

EXAMPLE 3

The procedure of Example 1 was followed except that in Step 5, 1-phenyl,1-(4-methoxyphenyl)-2-propyn-1-ol was used in place of 1,1-diphenyl-2-propyn-1-ol and a 1:9 mixture of ethyl acetate/hexanes was used as eluant to produce the desired product. NMR analysis showed the product to have a structure consistent with 3-(4-methoxyphenyl)-3,9-diphenyl-3H-9H-indeno[3',2':3,4]naphtho[1,2-b]pyran.

EXAMPLE 4

The procedure of Example 1 was followed except that in Step 5, 1-phenyl,1-(4-morpholinophenyl)-2-propyn-1-ol was used in place of 1,1-diphenyl-2-propyn-1-ol and a 1:9 mixture of ethyl acetate/hexanes was used as eluant to produce the desired product. NMR analysis showed the product to have a structure consistent with 3-(4-morpholinophenyl)-3,9-diphenyl-3H-9H-indeno[3',2':3,4]naphtho[1,2-b]pyran.

EXAMPLE 5

The procedure of Example 1 was followed except that in Step 1, 3-methoxybenzoyl chloride was used in place of benzoyl chloride and in Step 2, 3-methoxyphenyl magnesium bromide was used in place of phenyl lithium and in Step 5, 1,1-bis(4-methoxyphenyl)-2-propyn-1-ol was used in place of 1,1-diphenyl-2-propyn-1-ol and a 5:4:1 mixture of hexanes/dichloromethane/ethyl acetate/was used as eluant to produce the desired product. NMR analysis showed the product to have a structure consistent with 3,3-di(4-methoxyphenyl)-9-(3-methoxyphenyl)-11-methoxy-3H-9H-indeno[3',2':3,4]naphtho[1,2-b]pyran.

EXAMPLE 6

The procedure of Example 5 was followed except that in Step 5, 1-phenyl,1-(4-methoxyphenyl)-2-propyn-1-ol was used in place of 1,1-diphenyl-2-propyn-1-ol and a 5:4:1 mixture of hexanes/dichloromethane/ethyl acetate/was used as eluant to produce the desired product NMR analysis showed the product to have a structure consistent with 3-(4-methoxyphenyl)-3-phenyl-9-(3-methoxyphenyl)-11-methoxy-3H-9H-indeno[3',2':3,4]naphtho[1,2-b]pyran.

EXAMPLE 7

The product of Example 6, 3-(4-methoxyphenyl)-3-phenyl-9-(3-methoxyphenyl)-11-methoxy-3H-9H-indeno[3',2':3,4]naphtho[1,2-b]pyran (0.53 gram) was added to a reaction flask containing 20 mL of anhydrous tetrahydrofuran. The reaction mixture was cooled to −78° C. n-Butyl lithium (2.5 M in hexanes, 1.6 mL) was added dropwise with stirring, under an atmosphere of nitrogen. An immediate color change from light brown to dark brown was observed The reaction mixture was stirred for 30 minutes, at which time methyl iodide (0.8 mL, 12.8 mmol) was added dropwise with stirring. The reaction mixture was stirred for 24 hours at ambient temperature. The solvents were removed under reduced pressure. The residue was treated with 20 mL of water. The organic solids were combined and separated by column chromatography using as the eluant a 15:4:1 mixture of hexanes/dichloromethane/ethyl acetate to yield 0.4 gram of a yellow solid product. The Proton and Carbon-13 NMR and MS analysis showed the product to have a structure consistent with 3-(4-methoxyphenyl)-3-phenyl-9-methyl-11-methoxy-9-(3-methoxyphenyl)-3H-9H-indeno[3',2':3,4]naphtho[1,2-b]pyran.

EXAMPLE 8

The procedure of Example 7 was followed except that 3,3-di(4-methoxyphenyl)-9-(3-methoxyphenyl)-11-methoxy-3H-9H-indeno[3',2':3,4]naphtho[1,2-b]pyran was used in place of 3-(4-methoxyphenyl)-3-phenyl-9-(3-methoxyphenyl)-3H-9H-indeno[3',2':3,4]naphtho[1,2-b]pyran to produce the desired product. The Proton and Carbon-13 NMR and MS analysis showed the product to have a structure consistent with 3,3-di(4-methoxyphenyl)-9-methyl-11-methoxy-9-(3-methoxyphenyl)-3H-9H-indeno[3',2':3,4]naphtho[1,2-b]pyran.

EXAMPLE 9

The procedure of Example 1 was followed except that in Step 1, 3-methoxybenzoyl chloride was used in place of benzoyl chloride and in Step 2, methyl magnesium chloride was used in place of phenyl lithium and in Step 5, 1,1-bis(4-methoxyphenyl)-2-propyn-1-ol was used in place of 1,1-diphenyl-2-propyn-1-ol to produce the desired product.

NMR analysis showed the product to have a structure consistent with 3,3-di(4-methoxyphenyl)-9-methyl-11-methoxy-3H-9H-indeno[3',2':3,4]naphtho[1,2-b]pyran.

EXAMPLE 10

The procedure of Example 7 was followed except that 3,3-di(4-methoxyphenyl)-9-methyl-11-methoxy-3H-9H-indeno[3',2':3,4]naphtho[1,2-b]pyran was used in place of 3-(4-methoxyphenyl)-3-phenyl-9-(3-methoxyphenyl)-3H-9H-indeno[3',2':3,4]naphtho[1,2-b]pyran to produce the desired product. The Proton and Carbon-13 NMR and MS analysis showed the product to have a structure consistent with 3,3-di(4-methoxyphenyl)-9,9-dimethyl-11-methoxy-3H-9H-indeno[3',2':3,4]naphtho[1,2-b]pyran.

EXAMPLE 11

The procedure of Example 10 was followed except that in Step 5, 1-(4-methoxyphenyl)-1-phenyl-2-propyn-1-ol was used in place of 1,1-diphenyl-2-propyn-1-ol to produce the desired product. NMR analysis showed the product to have a structure consistent with 3-(4-methoxyphenyl)-3-phenyl-9,9-dimethyl-11-methoxy-3H-9H-indeno[3',2':3,4]naphtho[1,2-b]pyran.

EXAMPLE 12

The procedure of Example 11 was followed except that in Step 1, 3-methoxybenzoyl chloride was used in place of benzoyl chloride and 1,6-dimethoxynaphthalene was used in place of 1-methoxynaphthalene to produce the desired product. NMR analysis showed the product to have a structure consistent with 3,3-di(4-methoxyphenyl)-9,9-dimethyl-7,11-dimethoxy-3H-9H-indeno[3',2':3,4]naphtho[1,2-b]pyran.

EXAMPLE 13

The procedure of Example 12 was followed except that in Step 5, 1-(4-methoxyphenyl)-1-phenyl-2-propyn-1-ol was used in place of 1,1-di(4-methoxyphenyl)-2-propyn-1-ol to produce the desired product. NMR analysis showed the product to have a structure consistent with 3-(4-methoxyphenyl)-3-phenyl-9,9-dimethyl-7,11-dimethoxy-3H-9H-indeno[3',2':3,4]naphtho[1,2-b]pyran.

EXAMPLE 14

The procedure of Example 12 was followed except that in Step 5, 1-(4-morpholinophenyl)-1-phenyl-2-propyn-1-ol was used in place of 1,1-di(4-methoxyphenyl)-2-propyn-1-ol to produce the desired product. NMR analysis showed the product to have a structure consistent with 3-(4-morpholinophenyl)-3-phenyl-9,9-dimethyl-7,11-dimethoxy-3H-9H-indeno[3',2':3,4]naphtho[1,2-b]pyran.

EXAMPLE 15

The procedure of Example 9 was followed except that in Step 1, 3,5-dimethoxybenzoyl chloride was used in place of benzoyl chloride to produce the desired product. NMR analysis showed the product to have a structure consistent with 3,3-di(4-methoxyphenyl)-9-methyl-11,13-dimethoxy-3H-9H-indeno[3',2':3,4]naphtho[1,2-b]pyran.

EXAMPLE 16

The procedure of Example 15 was followed except that in Step 5, 1-(4-methoxyphenyl)-1-phenyl-2-propyn-1-ol was used in place of 1,1-di(4-methoxyphenyl)-2-propyn-1-ol to produce the desired product. NMR analysis showed the product to have a structure consistent with 3-(4-methoxyphenyl)-3-phenyl-9-methyl-11,13-dimethoxy-3H-9H-indeno[3',2':3,4]naphtho[1,2-b]pyran.

EXAMPLE 17

The procedure of Example 11 was followed except that in Step 1, 1-naphthoyl chloride was used in place of 3-methoxybenzoyl chloride to produce the desired product. NMR analysis showed the product to have a structure consistent with 3-(4-methoxyphenyl)-3-phenyl-9,9-dimethyl-3H-9H-benzo[4",5"]indeno[3',2':3,4]naphtho[1,2-b]pyran.

EXAMPLE 18

The procedure of Example 10 was followed except that in Step 1, 3-fluorobenzoyl chloride was used in place of 3-methoxybenzoyl chloride to produce the desired product. NMR analysis showed the product to have a structure consistent with 3,3-di(4-methoxyphenyl-9,9-dimethyl-11-fluoro-3H-9H-indeno[3',2':3,4]naphtho[1,2-b]pyran.

COMPARATIVE EXAMPLE 1

The procedure of Comparative Example 1 of U.S. Pat. No. 5,645,767 was followed. An NMR spectrum showed the product to have a structure consistent with 2,2-di(4-methoxyphenyl), 5-methoxycarbonyl,6-phenyl-[2H]-naphtho[1,2-b]pyran.

EXAMPLE 19

Part A

Testing was done with the photochromic compounds described in Examples 1 through 15, 17 and 18 and Comparative Example 1 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Testing of the photochromic properties of Example 16 was done as follows. A portion of the product was incorporated into (diglyme) diethylene glycol dimethyl ether and irradiated with long wave ultraviolet light. The color of the sample changed from clear to brown. After the irradiation was stopped, the color of the sample changed from brown to clear.

Part B

The photochromic test squares of Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm2). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where % Ta is the percent transmittance in the activated state and the logarithm is to the base 10. LABTECH NOTEBOOKpro software was used for all calculations.

The optical properties of the photochromic compounds in the test squares are reported in Table 1. The $\Delta OD$/Min, which represents the sensitivity of the photochromic compound's response to UV light, was measured over the first five (5) seconds of UV exposure, then expressed on a per minute basis. The saturation optical density ($\Delta OD$ @Saturation) was taken under identical conditions as the $\Delta OD$/Min, except UV exposure was continued for 15 minutes.

The lambda max (Vis) is the wavelength in the visible spectrum at which the maximum absorption of the activated (colored) form of the photochromic compound in a test square occurs. The lambda max (Vis) wavelengths reported in Table 1 were determined by testing the photochromic test square polymerizates of Part A in a Varian Cary 3 uv-visible spectrophotometer. The bleach rate (T ½) is the time interval in seconds for the absorbance of the activated form of the photochromic compound in the test squares to read one half the highest absorbance at room temperature (72° F., 22.2° C.) after removal of the source of activating light.

Each of the compounds of the Examples and the Comparative Example exhibited dual peak absorptions in the visible spectrum (lambda max visible) in distinct color regions. For the highest lambda max visible (Band B), the corresponding optical density ($\Delta OD$/Min and $\Delta OD$ at saturation) and bleach rate (T ½) for the desired compounds of the Examples and Comparative Example are tabulated in Table 1.

TABLE 1

| Compound Example | | Sensitivity $\Delta OD$/MIN | $\Delta OD$ @ Saturation | Bleach Rate T ½ sec | λ MAX (nm) Vis |
|---|---|---|---|---|---|
| 1 | (Band A) | | | | 416 |
| 1 | (Band B) | 0.12 | 0.30 | 147 | 516 |
| 2 | (Band A) | | | | 440 |
| 2 | (Band B) | 0.15 | 0.13 | 42 | 534 |
| 3 | (Band A) | | | | 433 |
| 3 | (Band B) | 0.16 | 0.25 | 88 | 527 |
| 4 | (Band A) | | | | 480 |
| 4 | (Band B) | 0.19 | 0.28 | 86 | 560 |
| 5 | (Band A) | | | | 447 |
| 5 | (Band B) | 0.16 | 0.16 | 52 | 550 |
| 6 | (Band A) | | | | 435 |
| 6 | (Band B) | 0.15 | 0.25 | 98 | 546 |
| 7 | (Band A) | | | | 435 |
| 7 | (Band B) | 0.17 | 0.24 | 90 | 547 |
| 8 | (Band A) | | | | 447 |
| 8 | (Band B) | 0.16 | 0.15 | 47 | 551 |
| 9 | (Band A) | | | | 445 |
| 9 | (Band B) | 0.17 | 0.15 | 47 | 550 |
| 10 | (Band A) | | | | 447 |
| 10 | (Band B) | 0.16 | 0.11 | 33 | 551 |
| 11 | (Band A) | | | | 434 |
| 11 | (Band B) | 0.16 | 0.19 | 66 | 548 |
| 12 | (Band A) | | | | 445 |
| 12 | (Band B) | 0.17 | 0.07 | 63 | 541 |
| 13 | (Band A) | | | | 430 |
| 13 | (Band B) | 0.13 | 0.23 | 153 | 533 |
| 14 | (Band A) | | | | 480 |
| 14 | (Band B) | 0.15 | 0.34 | 148 | 543 |
| 15 | (Band A) | | | | 441 |
| 15 | (Band B) | 0.10 | 0.05 | 24 | 546 |
| 17 | (Band A) | | | | 430 |
| 17 | (Band B) | 0.09 | 0.04 | 44 | 536 |
| 18 | (Band A) | | | | 441 |
| 18 | (Band B) | 0.16 | 0.10 | 39 | 535 |
| CE1 | (Band A) | | | | 422 |
| CE2 | (Band B) | 0.18 | 0.22 | 56 | 518 |

The results of Table 1 show that the compounds of Examples 1–15, 17 and 18 demonstrated acceptable photochromic properties, e.g., sensitivity, optical density at saturation and bleach rate A comparison of the data for the compounds of Examples 2, 5, 8, 9, 10, 12, 15 and 18 which have the same B and B' substituents as Comparative Example 1, to Comparative Example 1 show a higher lambda max for both Bands A and B and a shorter bleach rate for each of the Example compounds. The higher lambda max values for the Example compounds demonstrate a bathochromic shift in the visible spectrum.

The present invention has been described with reference to specific details of particular embodiments thereof. It is not intended that such details be regarded as limitations upon the scope of the invention.

We claim:
1. A naphthopyran compound represented by the following graphic formula:

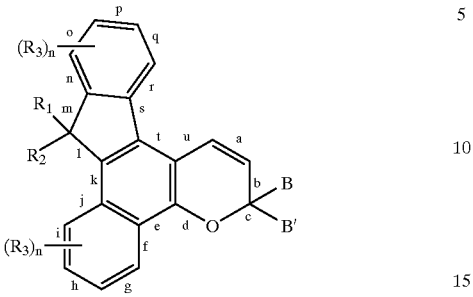

wherein,
(a) $R_1$ and $R_2$ are each selected from the group consisting of:
  (i) hydrogen, hydroxy, amino, mono- and di-substituted amino, $C_1$–$C_6$ alkyl, $C_1$–$C_6$ haloalkyl, $C_3$–$C_7$ cycloalkyl, allyl, benzyl, mono-substituted benzyl, halogen and the group, —C(O)W, wherein W is hydroxy, $C_1$–$C_6$ alkyl, $C_1$–$C_6$ alkoxy, phenyl, $C_3$–$C_7$ cycloalkyloxy, mono-substituted phenyl, phenoxy, amino, mono($C_3$–$C_7$)alkylamino, di ($C_1$–$C_6$) alkylamino, morpholino, piperidino or pyrrolidyl, said amino substituents being selected from the group consisting of $C_1$–$C_6$ alkyl, phenyl, benzyl and naphthyl, said benzyl and phenyl substituents being $C_1$–$C_6$ alkyl, $C_1$–$C_6$ alkoxy, piperidino, morpholino, di($C_1$–$C_6$)alkylamino or fluoro;
  (ii) unsubstituted, mono- di- and tri-substituted members selected from the group consisting of phenyl, naphthyl, phenanthryl, pyrenyl, quinolyl, isoquinolyl, benzofuranyl, thienyl, benzothienyl, dibenzofuranyl, dibenzothienyl, carbazolyl, and indolyl, said group substituents in (a) (ii) being selected from the group consisting of halogen, $C_1$–$C_6$ alkyl, $C_1$–$C_6$ alkoxy, morpholino, pipenidino, pyrrolidino, amino, mono- and di-substituted amino, said amino substituents being selected from the group consisting of $C_1$–$C_6$ alkyl, phenyl, benzyl and naphthyl;
  (iii) monosubstituted phenyl, having a substituent at the para position that is a linking group, —(CH$_2$)$_t$— or —O—(CH$_2$)$_t$—, wherein t is the integer 1, 2, 3, 4, 5 or 6, connected to an aryl group, which is a member of another photochromic naphthopyran;
  (iv) a group, —OR$_5$, wherein R$_5$ is $C_1$–$C_6$ alkyl, $C_1$–$C_6$ acyl, phenyl ($C_1$–$C_3$)alkyl, mono ($C_1$–$C_6$)alkyl substituted phenyl ($C_1$–$C_3$)alkyl, mono($C_1$–$C_6$)alkoxy substituted phenyl($C_1$–$C_3$)alkyl, $C_1$–$C_6$ alkoxy ($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ haloalkyl, allyl, benzoyl, monosubstituted benzoyl, naphthoyl or monosubstituted naphthoyl, said benzoyl and naphthoyl group substituents being $C_1$–$C_6$ alkyl or $C_1$–$C_6$ alkoxy; or R$_5$ is the group —CH(R$_6$)Q, wherein R$_6$ is hydrogen or $C_1$–$C_3$ alkyl and Q is —CN, —CF$_3$, or —COOR$_7$, and R$_7$ is hydrogen or $C_1$–$C_3$ alkyl; or R$_5$ is the group, —C(O)V, wherein V is hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group, amino, mono($C_1$–$C_6$) alkylamino, di($C_1$–$C_6$)alkylamino phenylamino, mono- or di-($C_1$–$C_6$)alkyl substituted phenylamino, or mono- or di-($C_1$–$C_6$) alkoxy substituted phenylamino, said aryl group substituents being $C_1$–$C_6$ alkyl or $C_1$–$C_6$ alkoxy;
  (v) a group, —CH(Q')$_2$, wherein Q' is —CN or —COOR$_8$, wherein R$_8$ is hydrogen, $C_1$–$C_6$ alkyl, phenyl($C_1$–$C_3$)alkyl, mono ($C_1$–$C_6$)alkyl substituted phenyl($C_1$–$C_3$)alkyl, mono($C_1$–$C_6$)alkoxy substituted phenyl($C_1$–$C_3$)alkyl, or an unsubstituted, mono- or di-substituted aryl group, each of said aryl group substituents being $C_1$–$C_6$ alkyl or $C_1$–$C_6$ alkoxy;
  (vi) a group, —CH(R$_9$)G, wherein R$_9$ is hydrogen, $C_1$–$C_6$ alkyl or an unsubstituted, mono- or di-substituted aryl group, and G is hydroxy, $C_1$–$C_6$ alkoxy, aryloxy, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino, —COOR$_8$, —COR$_{10}$ or —CH$_2$OR$_{11}$, wherein R$_{10}$ is hydrogen, $C_1$–$C_6$ alkyl, an unsubstituted, mono- or di-substituted aryl group, amino, mono($C_1$–$C_6$) alkylamino, di($C_1$–$C_6$) alkylamino, phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_3$) alkyl substituted diphenylamino, mono- or di($C_1$–$C_6$)alkoxy substituted diphenylamino, morpholino, or piperidino, wherein R$_{11}$ is hydrogen, —C(O)R$_8$, $C_1$–$C_6$ alkyl, $C_1$–$C_3$ alkoxy($C_1$–$C_6$)alkyl, phenyl($C_1$–$C_3$)alkyl, mono($C_1$–$C_6$) alkoxy substituted phenyl($C_1$–$C_3$)alkyl, or an unsubstituted, mono- or di-substituted aryl group, each of said aryl group substituents being $C_1$–$C_6$ alkyl or $C_1$–$C_6$ alkoxy; and
  (vii) a group, T, represented by the formula:

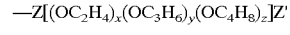

or

wherein —z is —C(O)— or —CH$_2$—, Z' is $C_1$–$C_3$ alkoxy or a polymerizable group, x, y and z are each a number between 0 and 50, and the sum of x, y and z is between 2 and 50; or
  (viii) R$_1$ and R$_2$ together form an oxo group, a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl, provided that said spiro-carbocyclic ring is not fluoren-9-ylidene;
(b) each R$_3$ is independently selected from the group consisting of hydrogen, $C_1$–$C_6$ alkyl, $C_1$–$C_6$alkoxy, $C_3$–$C_7$ cycloalkyl, phenyl, benzyl, di ($C_1$–$C_6$) alkylamino, dicyclohexylamine, diphenylamino, piperidyl, morpholinyl, pyridyl, halogen, a group, T, and the group —C(O)W and n is the integer 0, 1, or 2; or when n is 2, and the R$_3$ substituents are adjacent, each pair of substituents independently forms a first R$_3$ and second R$_3$ substituted or unsubstituted fused carbocyclic or heterocyclic ring selected from the group consisting of benzo, pyridino, pyrazino, pyrimidino, furano, dihydrofurano, 1,3-dioxolo, 1,4-dioxolo, 1,3-dioxino, 1,4-dioxino, thiopheno, benzofuro, benzothieno, indolo, and indeno, the substituents of said fused carbocyclic or heterocyclic ring being selected from the group consisting of halogen, $C_1$–$C_6$ alkyl, $C_1$–$C_6$ alkoxy, amino, mono- and di-substituted amino, said amino substituents being selected from the group consisting of $C_1$–$C_6$ alkyl, phenyl, benzyl and naphthyl; said first $R_3$ ring being fused to the o, p or q side and said second $R_3$ ring being fused to the g, h or i side of the naphthopyran;

(c) B and B' are each selected from the group consisting of:
  (i) mono-T-substituted phenyl
  (ii) an unsubstituted, mono-, di-, and tri-substituted aryl group;
  (iii) 9-julolidinyl and an unsubstituted, mono- or di-substituted heteroaromatic group selected from the group consisting of pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and heteroaromatic substituents in (c) (ii) and (iii) being selected from the group consisting of hydroxy, aryl, hydroxy, aryl, mono ($C_1$–$C_6$)alkoxyaryl, di($C_1$–$C_6$)alkoxyaryl, mono ($C_1$–$C_6$)alkylaryl, di($C_1$–$C_6$)alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl ($C_1$–$C_6$)alkoxy, aryloxy, aryloxy($C_1$–$C_6$) alkyl, aryloxy($C_1$–$C_6$)alkoxy, mono- and di-($C_1$–$C_6$) alkylaryl($C_1$–$C_6$)alkyl mono- and di-($C_1$–$C_6$) alkoxyaryl($C_1$–$C_6$)alkyl, mono- and di-($C_1$–$C_6$) alkylaryl($C_1$–$C_6$)alkoxy, mono- and di-($C_1$–$C_6$) alkoxyaryl($C_1$–$C_6$)alkoxy, amino, mono($C_1$–$C_6$) alkylamino, di($C_1$–$C_6$)alkylamino, diarylamino, piperazino, N—($C_1$–$C_6$)alkylpiperazino, N-arylpiperazino, aziridino, indolino, piperidino, morpholino, thiomorpholino, tetrahydroquinolino, tetrahydroisoquinolino, pyrryl, pyrrolidyl, $C_1$–$C_6$ alkyl, $C_1$–$C_6$ haloalkyl, $C_1$–$C_6$ alkoxy, mono($C_1$–$C_6$) alkoxy($C_1$–$C_4$) alkyl, acryloxy, methacryloxy and halogen;
  (iv) an unsubstituted or mono-substituted member selected from the group consisting of pyrazolyl, imidazolyl, pyrazolinyl, imidazolinyl, pyrrolinyl, phenothiazinyl, phenoxazinyl, phenazinyl and acridinyl, each of said substituents being selected from the group consisting of $C_1$–$C_6$ alkyl, $C_1C_6$ alkoxy, phenyl, and halogen;
  (v) monosubstituted phenyl, having a substituent at the para position that is a linking group, —($CH_2$)$_t$— or —O—($CH_2$)$_t$—, wherein t is the integer 1, 2, 3, 4, 5 or 6, connected to an aryl group, which is a member of another photochromic naphthopyran;
  (vi) a group represented by one of the following graphic formula:

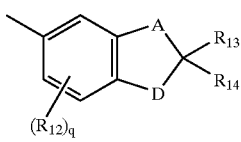 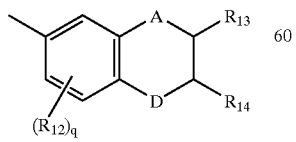

wherein A is methylene or oxygen and D is oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{12}$ is $C_1$–$C_6$ alkyl, $C_1$–$C_6$ alkoxy, hydroxy, or halogen; $R_{13}$ and $R_{14}$ are each hydrogen or $C_1$–$C_6$ alkyl; and q is the integer 0, 1, or 2;
  (vii) $C_1$–$C_6$ alkyl, $C_1$–$C_6$ haloalkyl, $C_1$–$C_6$ alkoxy ($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl ($C_3$–$C_6$)-cycloalkyl, halo($C_3$–$C_6$)cycloalkyl, and $C_4$–$C_{12}$ bicycloalkyl; and
  (viii) a group represented by the following graphic formula:

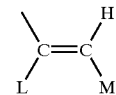

wherein L is hydrogen or $C_1$–$C_4$ alkyl and M is selected from the unsubstituted, mono-, and di-substituted members of the group consisting of naphthyl, phenyl, furanyl, and thienyl, each of said group substituents being $C_1$–$C_4$ alkyl, $C_1$–$C_4$alkoxy, or halogen; or
(d) B and B' taken together form fluoren-9-ylidene, mono-, or di-substituted fluoren9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_{1\ -C4}$ alkyl, $C_1$–$C_4$ alkoxy, and halogen; said halogen or halo group herein being bromo, chloro, fluoro or iodo and said aryl groups herein being phenyl or naphthyl.

2. A naphthopyran compound of claim 1 wherein,
(a) $R_1$ and $R_2$ are each selected from the group consisting of:
  (i) hydrogen, hydroxy, $C_1$–$C_6$ alkyl, $C_1$–$C_6$ haloalkyl, di-substituted amino, $C_3$–$C_7$ cycloalkyl, benzyl, mono-substituted benzyl, and the group, —C(O)W, wherein W is $C_1$–$C_6$ alkoxy, di($C_1$–$C_6$)alkylamino, morpholino, or piperidino, said amino substituents being $C_1$–$C_6$ alkyl, said benzyl substituents being $C_1$–$C_6$ alkyl or $C_1$–$C_6$ alkoxy;
  (ii) mono- di- and tri-substituted members selected from the group consisting of phenyl, naphthyl, and dibenzofuranyl, said group substituents in (a) (ii) being selected from the group consisting of $C_1$–$C_6$ alkyl, $C_1$–$C_6$ alkoxy, di-substituted amino, said amino substituents being $C_1$–$C_6$ alkyl;
  (iii) mono-substituted phenyl, having a substituent at the para position that is a linking group, —O—($CH_2$)$_t$—, wherein t is the integer 3, 4, or 5, connected to an aryl group, which is a member of another photochromic naphthopyran;
  (iv) a group, —$OR_5$, wherein $R_5$ is $C_1$–$C_6$ alkyl, $C_1$–$C_6$ acyl, $C_1$–$C_6$ alkoxy($C_2$–$C_4$)alkyl, benzoyl, or mono-substituted benzoyl, said benzoyl group substituents being $C_1$–$C_6$ alkyl or $C_1$–$C_6$ alkoxy; or $R_5$ is the group —CH($R_6$)Q, wherein $R_6$ is hydrogen and Q is —$COOR_7$, and $R_7$ is $C_1$–$C_3$ alkyl; or $R_5$ is the group, —C(O)V, wherein V is $C_1$–$C_6$ alkoxy, or di($C_1$–$C_6$) alkylamino;
  (v) a group, —CH(Q')$_2$, wherein Q' is —$COOR_8$, wherein $R_8$ is $C_1$–$C_6$ alkyl, or phenyl($C_1$–$C_3$)alkyl;

(vi) a group, —CH(R$_9$)G, wherein R$_9$ is (C$_1$–C$_6$)alkyl, and G is C$_1$–C$_6$ alkoxy, —COOR$_8$, or —CH$_2$OR$_{11}$, wherein R$_{10}$ is C$_1$–C$_6$ alkyl, di(C$_1$C$_6$)alkylamino, morpholino, or piperidino, wherein R$_{11}$ is C$_1$–C$_6$ alkyl, or C$_1$–C$_3$ alkoxy(C$_1$–C$_6$)alkyl; and (vii) a group, T, represented by the formula:

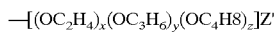

wherein Z' is C$_1$–C$_3$ alkoxy or a polymerizable group, x, y and z are each a number between 0 and 50, and the sum of x, y and z is between 2 and 50; or (viii) R$_1$ and R$_2$ together form an oxo group, or a substituted or unsubstituted spiro-heterocyclic group containing 1 or 2 oxygen atoms and 3 to 6 carbon atoms including the spirocarbon atom, said spiro-heterocyclic group being annellated with 1 or 2 benzene rings, said substituents being or C$_1$–C$_6$ alkyl;

(b) each R$_3$ is independently selected from the group consisting of hydrogen, C$_1$–C$_6$ alkyl, C$_1$–C$_6$ alkoxy, di(C$_1$–C$_6$)alkylamino, piperidyl, morpholinyl, pyrrolidyl, halogen, a group, T, and the group —C(O)W and n is the integer 0, 1, or 2, or when n is 2, and the R$_3$ substituents are adjacent, a pair of substituents independently forms a substituted or unsubstituted fused carbocyclic or heterocyclic R$_3$ ring selected from the group consisting of benzo, dihydrofurano and benzofuro, the substituents of said fused carbocyclic or heterocyclic ring being selected from the group consisting of C$_1$–C$_6$ alkyl, C$_1$–C$_6$ alkoxy, and di-substituted amino, said amino substituents being C$_1$–C$_6$ alkyl; said R$_3$ ring being fused to the o, p or q side of the naphthopyran;

(c) B and B' are each selected from the group consisting of:
 (i) a mono-, or di-substituted phenyl group;
 (ii) an unsubstituted, mono- or di-substituted heteroaromatic group selected from the group consisting of furanyl, benzofuran-2-yl, thienyl, benzothien-2-yl, and dibenzofuranyl, each of said phenyl and heteroaromatic substituents in (c) (i) and (ii) being selected from the group consisting of hydroxy, amino, mono(C$_1$–C$_6$)alkylamino, di(C$_1$–C$_6$) alkylamino, piperidino, morpholino, pyrryl, C$_1$–C$_3$ alkyl, C$_1$–C$_3$ chloroalkyl, C$_1$C$_3$ fluoro-alkyl, C$_1$C$_3$ alkoxy, mono(C$_1$–C$_3$)alkoxy(C$_1$–C$_3$)alkyl, fluoro and chloro;
 (iii) a group represented by one of the following graphic formula:

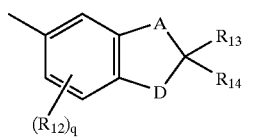 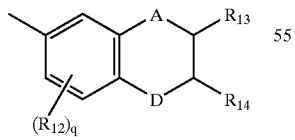

wherein A is methylene and D is oxygen; each R$_{12}$ is C$_1$–C$_3$ alkyl, or C$_1$–C$_3$ alkoxy; R$_{13}$ and R$_{14}$ are each hydrogen or C$_1$–C$_4$ alkyl; and q is the integer 0, or 1;
 (iv) C$_1$–C$_4$ alkyl,
 (v) a group represented by the following graphic formula:

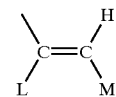

wherein L is hydrogen or methyl and M is phenyl or selected mono-, substituted phenyl, said phenyl substituent being C$_1$–C$_3$ alkyl, C$_1$–C$_3$ alkoxy, or fluoro; or (d) B and B' taken together form fluoren-9-ylidene, monosubstituted fluoren-9-ylidene or a member selected from the group consisting of saturated C$_3$–C$_8$ spiro-monocyclic hydrocarbon rings, saturated C$_7$–C$_{10}$ spiro-bicyclic hydrocarbon rings, and saturated C$_7$–C$_{10}$ spiro-tricyclic hydrocarbon rings, said fluoren-9-ylidene substituent being selected from the group consisting of C$_1$–C$_3$ alkyl, C$_1$–C$_3$ alkoxy, fluoro and chloro.

3. A naphthopyran compound of claim 2 wherein:
(a) R$_1$ and R$_2$ are each selected from the group consisting of:
 (i) hydrogen, hydroxy, C$_1$–C$_3$ alkyl, and the group, —C(O)W, wherein W C$_1$–C$_6$ alkoxy, or morpholino;
 (ii) unsubstituted, and mono-substituted phenyl, said phenyl substituents in (a) (ii) being selected from the group consisting of C$_1$–C$_6$ alkoxy, and di-substituted amino, said amino substituents being of C$_1$–C$_3$ alkyl,
 (iii) monosubstituted phenyl, having a substituent at the para position that is a linking group, —O—(CH$_2$)$_t$— wherein t is the integer 3, connected to an aryl group, which is a member of another photochromic naphthopyran;
 (iv) a group, —OR$_5$, wherein R$_5$ is C$_1$–C$_6$ alkyl, C$_1$C$_6$ alkoxy(C$_2$–C$_4$)alkyl the group —CH(R$_6$)Q, wherein R$_6$ is hydrogen or C$_1$C$_3$ alkyl and Q is —COOR$_7$, and R$_7$ is C$_1$–C$_3$ alkyl; or R$_5$ is the group, —C(O)V, wherein V is C$_1$–C$_6$ alkoxy;
 (v) a group, —CH(Q')$_2$, wherein Q' is —COOR$_8$, wherein R$_8$ is C$_1$–C$_6$ alkyl.
 (vi) a group, —CH(R$_9$)G, wherein R$_9$ is C$_1$–C$_6$ alkyl and G is C$_1$–C$_6$ alkoxy, —COOR$_8$, —COR$_{10}$ or —CH$_2$OR$_{11}$, wherein R$_{10}$ and R$_{11}$ are each C$_1$–C$_6$ alkyl; and
 (vii) a group, T, represented by the formula:

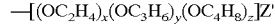

wherein Z' is C$_1$–C$_3$ alkoxy or a polymerizable group, x, y and z are each a number between 0 and 50, and the sum of x, y and z is between 2 and 50; or
 (viii) R$_1$ and R$_2$ together form an oxo group, a substituted or unsubstituted spiro-heterocyclic group containing 1 oxygen atom and 6 carbon atoms including the spirocarbon atom, said spiro-heterocyclic group being annellated with 2 benzene rings, said substituents being C$_1$–C$_3$ alkyl;

(b) each R$_3$ is independently selected from the group consisting of hydrogen, C$_1$–C$_6$ alkyl, C$_1$–C$_6$ alkoxy, morpholinyl, a group, T, and the group —C(O)W and n is the integer 0, 1, or 2, or when n is 2, and the R$_3$ substituents are adjacent, the pair of substituents independently forms a substituted or unsubstituted fused carbocyclic or heterocyclic R$_3$ ring selected from the group consisting of benzo, and benzofuro, the substituents of said fused carbocyclic or heterocyclic ring being $C_1$–$C_6$ alkoxy; said $R_3$ ring being fused to the p side of the naphthopyran;
(c) B and B' are each selected from the group consisting of:
(i) an unsubstituted, mono-, or di-substituted phenyl group;
(ii) an unsubstituted, mono- or di-substituted heteroaromatic group selected from the group consisting of furanyl, benzofuran-2-yl, thienyl, benzothien-2-yl, and dibenzofuranyl, each of said phenyl and heteroaromatic substituents in (c) (i) and (ii) being selected from the group consisting of hydroxy, piperidino, morpholino, $C_1$–$C_3$ alkyl, and $C_1$–$C_3$ alkoxy;
(iii) a group represented by the following graphic formula:

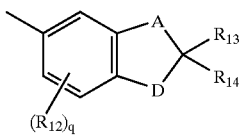

wherein A is methylene and D is oxygen; each $R_{12}$ is $C_1$–$C_3$ alkyl, or $C_1$–$C_3$ alkoxy; $R_{13}$ and $R_{14}$ are each hydrogen or $C_1$–$C_3$ alkyl; and q is the integer 0, or 1; or
(d) B and B' taken together form fluoren-9-ylidene, adamantylidene, bornylidene, norbornylidene, or bicyclo nonan-9-ylidene.

4. A naphthopyran compound selected from:
(a) 3,3,9-triphenyl-3H-9H -indeno[3'2':3,4]naphtho[1,2-b]pyran;
(b) 3,3-di (4-methoxyphenyl)-9-phenyl-3H-9H-indeno[3',2':3,4]naphtho[1,2b]pyran;
(c) 3-(4-methoxyphenyl)-3, 9-diphenyl-3H-9H-indeno[3',2':3,4]naphtho[1,2-b]pyran;
(d) 3-(4morpholinophenyl)-3, 9-diphenyl-3H-9H-indeno[3',2':3,4]naphtho[1,2b]pyran;
(e) 3,3-di(4-methoxyphenyl)-9-(3-methoxyphenyl)-11-methoxy-3H-9H-indeno[3',2':3,4]naphtho[1,2-b]pyran;
(f) 3-(4-methoxyphenyl)-3-phenyl-9-(3-methoxyphenyl)-11-methoxy-3H-9H-indeno[3',2':3,4]naphtho[1,2-b]pyran;
(g) 3-(4-methoxyphenyl)-3-phenyl-9-methyl-11-methoxy-9-(3-methoxyphenyl)-3H-9H-indeno[3',2':3,4]naptho[1,2-b]pyran;
(h) 3,3di-(4-methoxyphenyl)-9-methyl-11-methoxy-9-(3-methoxyphenyl)-3H-9H-indeno[3',2':3,4]naptho[1,2-b]pyran;
(i) 3,3-di(4-methoxyphenyl)-9-methyl-11-methoxy-3H-9H-indeno[3',2':3,4]naphtho[1,2-b]pyran;
(j) 3,3-di(4-methoxyphenyl)-9,9-dimethyl-11-methoxy-3H-9H-indeno[3',2':3,4]naphtho[1,2-b]pyran;
(k) 3-(4-methoxyphenyl)-3-phenyl-9,9-dimethyl-11-methoxy-3H-9H-indeno[3',2':3,4]naphtho[1,2-b]pyran;
(l) 3,3di-(4-methoxyphenyl)-9,9-dimethyl-7,11-dimethoxy-3H-9H-indeno[3',2':3,4]naphtho[1,2--b]pyran;
(m) 3-(4-methoxyphenyl)-3-phenyl-9,9-dimethyl-7,11-dimethoxy-3H-9H-indeno[3',2':3,4]naphtho[1,2-b]pyran;
(n) 3-(4-morpholinophenyl)-3-phenyl-9,9-dimethyl-7,11-dimethoxy-3H-9H-indeno[3',2':3,4]naphtho[1,2-b]pyran;
(o) 3,3-di(4-methoxyphenyl)-9-methyl-11,13-dimethoxy-3H-9H-indeno[3',2':3,4]naphtho[1,2-b]pyran;
(p) 3-(4-methoxyphenyl)-3-phenyl-9-methyl-11,13-dimethoxy-3H-9H-indeno[3',2':3,4]naphtho[1,2-b] pyran;
(q) 3-(4-methoxyphenyl)-3-phenyl-9,9-dimethyl-3H-9H-benzo[4",5"]indeno[3',2':3,4]naphtho[2-b]pyran; and
(r) 3,3-di(4-methoxyphenyl-9,9-dimethyl-11-fluoro3H-9H-indeno[3',2':3,4]naphtho[1,2-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly (ethylene terephthalate), polystyrene, poly(alpha methylstyrene), copoly(styrene-methylmethacrylate) copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

7. The photochromic article of claim 6 wherein the polymeric organic host material is a solid transparent polymer selected from the group consisting of poly (methyl methacrylate), poly(ethylene glycol bismethacrylate), poly (ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, dilsopropenyl benzene monomers and ethoxylated trimethylol propane triacrylate monomers.

8. The photochromic article of claim 7 wherein the photochromic compound is present in an amount of from 0.05 to 2.0 milligram per square centimeter of organic host material surface to which the photochromic substance(s) is incorporated or applied.

9. The photochromic article of claim 8 wherein said article is a lens.

10. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 12 wherein the polymerizate is an optical element.

15. The photochromic article of claim 14 wherein said optical element is an ophthalmic lens or a contact lens.

16. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

17. The photochromic article of claim 16 wherein the polymeric organic host material is a solid transparent homopolymer or copolymer selected from the group consisting of poly(methyl methacrylate), poly(ethylene glycol bis-methacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

18. The photochromic article of claim 16 wherein the organic photochromic compound (b) is selected from the group consisting of naphthopyrans, benzopyrans, phenanthropyrans, indenonaphthopyrans, oxazines, organo-metal dithizonates, fulgides, fulgimides, spiro(indoline) pyrans and mixtures thereof.

19. The photochromic article of claim 18 wherein the total amount of photochromic compound present is from 0.05 to 1.0 milligram per square centimeter of organic host material surface to which the photochromic substance(s) is incorporated or applied.

20. The photochromic article of claim 19 wherein the article is an ophthalmic lens on a contact lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *